United States Patent [19]

Hernandez

[11] Patent Number: 5,106,365
[45] Date of Patent: Apr. 21, 1992

[54] MICRODIALYSIS PROBE

[75] Inventor: Luis Hernandez, Toulouse, France

[73] Assignee: Europhor SA, Toulouse, France

[21] Appl. No.: 539,073

[22] Filed: Jun. 15, 1990

[30] Foreign Application Priority Data

Jun. 16, 1989 [FR] France ................... 89 08013

[51] Int. Cl.$^5$ .............................................. A61B 5/03
[52] U.S. Cl. ........................................ 604/27; 128/632; 128/760
[58] Field of Search ................ 604/27, 29; 128/632, 128/760

[56] References Cited

U.S. PATENT DOCUMENTS 4,694,832 9/1987 Ungerstedt ...................... 128/632
4,772,269 9/1988 Twardowski et al. ............ 604/29 X

FOREIGN PATENT DOCUMENTS 1595079 10/1977 United Kingdom .

OTHER PUBLICATIONS

J. M. R. Delgado et al., "Dialytrode Technology and Local Profiles of Amino Acids in the Awake Cat Brain", J. Neurochem. 42, 1218-1228 12(1984).
J. M. R. Delgado et al., "Use of Dialytrodes in Brain Neurochemistry", Academic Press, Inc., 95-117 (1985) 12-1985.

Primary Examiner—William H. Grieb
Attorney, Agent, or Firm—Gottlieb, Rackman & Reisman

[57] ABSTRACT

A microdialysis probe comprising an outer sleeve containing tubes for delivering and removing dialysis products. The dialysis membrane is directly fixed to the end edge of the outer sleeve by gluing the membrane in such a manner as to avoid extra thickness at the junction between the membrane and the sleeve.

5 Claims, 1 Drawing Sheet

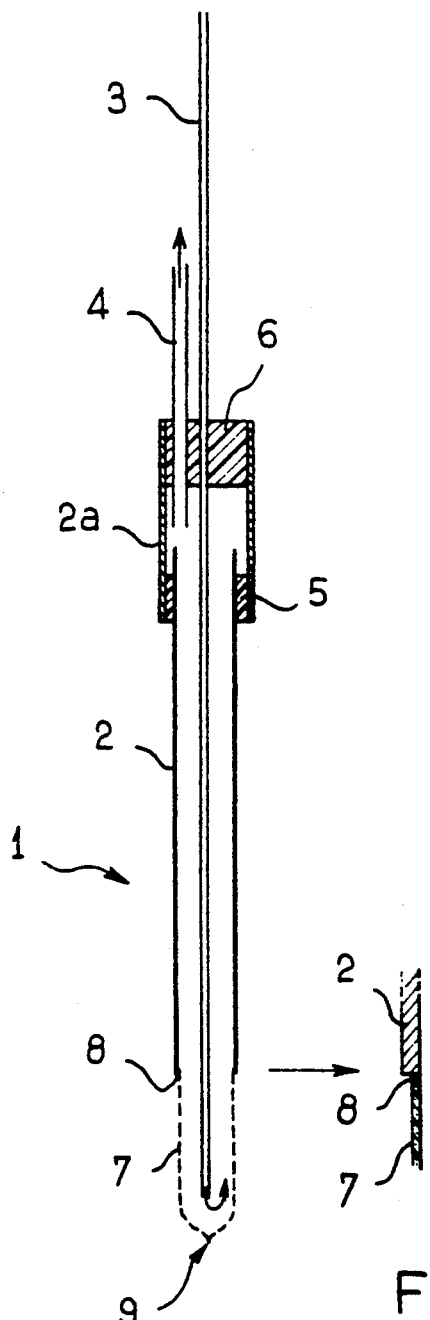
FIG. 1
FIG. 1a
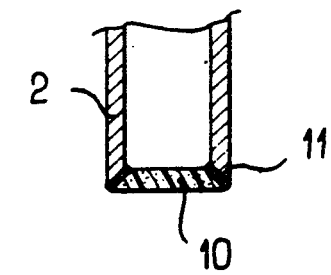
FIG. 2
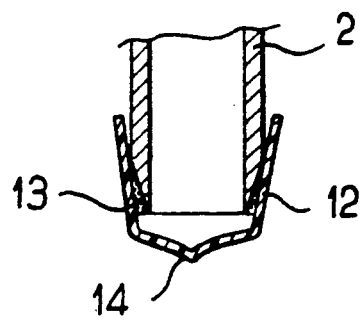
FIG. 3
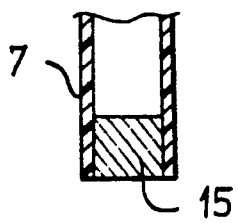
FIG. 4

MICRODIALYSIS PROBE

The invention relates to a microdialysis probe intended essentially for insertion into biological tissue, and more particularly into brain tissue.

BACKGROUND OF THE INVENTION

The dialysis phenomenon is used in the medical and biological field either for taking samples of substances secreted in living tissue in order to analyze the substances for diagnostic purposes, or else to deliver a drug or a medicine to living tissue. The dimensions of the dialysis probe must naturally be small so as to avoid damaging biological tissue, and this is of major importance when working on brain tissue. That is why the present invention relates more specifically to microdialysis.

Presently available microdialysis probes comprise two parallel or concentric dialysis tubes with their distal ends that come into contact with biological tissue being provided either with an external protection device (cf. GB-A-1 595 079, for example) or else with a mount which surrounds the dialysis membrane (FR-A-2 537 000).

Such devices for protecting the membrane which is itself very fine and fragile suffer from the drawback of damaging biological tissue since they cannot be made with small dimensions for reasons relating both to problems of making such protection devices and to problems of fixing the membrane which must naturally be fixed in a manner which is perfecting reliable.

SUMMARY OF THE INVENTION

The invention solves the problem by providing a microdialysis probe of the type including an external sleeve containing the tube for delivering and removing substances, the probe not requiring any external protective device nor any mount surrounding the dialysis membrane, while still making it possible to use a fine membrane.

In such a probe the dialysis membrane is fixed directly to the end edge of the external sleeve by gluing the membrane thereto, thereby avoiding any increase in thickness at the join between the membrane and the sleeve. There is thus no crushing of living tissue beyond that which is strictly required for passing the active portion of the probe.

In a first embodiment, the sleeve has an internal chamfer and the membrane is fixed by gluing, e.g. using epoxy resin, with the membrane being cut out and put into place by a punching technique whereby the glue-covered chamfered end of the sleeve is inserted into a sheet of membrane.

In a second embodiment, a tubular length of membrane is glued to extend the optionally chamfered end of the sleeve, after which the free end of the tubular length is closed, e.g. by heat sealing or by plugging with epoxy or other resin.

In a third embodiment, a tubular length of membrane is threaded over a sleeve having an external chamfer, with or without glue depending on the threaded-over length, and the free end is closed as above by heat sealing or by a plug.

Such embodiments have the advantage of being easy to make while enabling probes of very small diameter to be fabricated. It is possible to make sleeves having a diameter lying in the range 100 $\mu$m or even less to 150 $\mu$m, whereas prior techniques could not go below 200 $\mu$m. In addition, when the membrane closes the end of the sleeve in plane manner (first embodiment), it is possible to perform microdialysis on contact with cells but without damaging them, and a particular application for this arises with the highly localized cell clusters or nucleii in the brain. Naturally, the use of a probe of very small size makes it possible to reach zones that are inaccessible for existing probes without causing damage, and also makes it possible to operate with very high accuracy both when delivering substance and when collecting substance. In conventional probes, the dialysis area is relatively large and dilution occurs in or by means of the ambient medium.

The membrane used may be dialysis membranes that perform selection on the basis of molecular weight and/or on the basis of any other suitable criterion (enzyme affinity, and sulfid group affinity, to name but two well-known examples).

BRIEF DESCRIPTION OF THE DRAWING

Embodiments of the invention are described by way of examples with reference to the accompanying drawing, in which:

FIG. 1 is a diagrammatic section through a dialysis probe incorporating an embodiment of the invention;

FIG. 1a is a detail of FIG. 1 on a larger scale showing how the membrane is mounted;

FIG. 2 is a diagrammatic section through a dialysis membrane mounted on a different embodiment of a probe;

FIG. 3 is a diagrammatic section through a third embodiment of a dialysis membrane; and FIG. 4 shows how a tubular membrane can be plugged with a plug of epoxy.

DETAILED DESCRIPTION

A dialysis probe 1 comprises a tubular sleeve 2 made of metal or of a plastic material (e.g. stainless steel, particularly when the end of the sleeve is chamfered) having a delivery tube 3 and a removal tube 4 (or vice versa) mounted therein, e.g. by means of a second sleeve 2a or larger diameter. These two tubes 3 and 4 may be made of metal, or the delivery tube may be a capillary tube of fused silica or of polyimide. The delivery tube 3 extends right up to the distal end of the probe, whereas the removal tube 4 opens out into the proximal end of the probe (with the opposite disposition also being possible), with sealing between the two sleeves 2 and 2a, and also between the tubes 3 and 4 and the sleeve 2a being provided by resin glue at 5 and 6, e.g. by epoxy resin. Naturally, the tubes 3 and 4 are connected to conventional feed and/or analysis devices (not shown) appropriate for the use to which the probe is being put (taking samples, perfusing medicines, etc. . . . ).

In the embodiment of FIGS. 1 and 1a, a length of tubular membrane 7 is glued at 8 (e.g. using an epoxy resin) to extend the sleeve 2. The membrane 7 has substantially the same inside diameter as the sleeve 2, but its outside diameter may be smaller, as shown. The free end of the length of membrane 7 is closed at 9 by heat sealing.

The membrane 7 is fixed to the sleeve 2 by putting the length of membrane and the sleeve into alignment with each other under a microscope, with one or other or both of them being previously coated in glue, they are then kept in contact for the time required by the resin to set, after which the open end is closed by hot clamping (heat sealing, 9, 14, FIGS. 1 and 3) or by means of a resin plug (e.g. an epoxy resin plug, 15, FIG. 4).

The end of the sleeve may be plane or chamfered on the inside or the outside in order to offer a larger gluing area with the membrane.

When a plug, e.g. an epoxy plug, is used, the plug may itself be chamfered, in particular when the probe is to be inserted into a blood vessel, so as to provide a cutting edge.

In another embodiment (FIG. 2) the end of the sleeve 2 has an internal chamfer and after being coated in glue, it is used as a punch in order to cut out a disk 10 from a sheet of membrane, thereby closing the open end of the sleeve, with the disk being held in place, e.g. by epoxy resin 11.

In yet another embodiment (FIG. 3) a length of membrane 12 is threaded over the end of the sleeve 2 which is shaped to have an external chamfer, and the membrane is held in place by being glued at 13 to the chamfer by means of resin, e.g. an epoxy resin. In some applications, it may be advantageous for the sleeve 2 in contact with biological tissue to be covered with a membrane, in which case the membrane 12 need merely be of sufficient length long beyond the chamfer of the sleeve 2. If the overlap of the membrane along the sleeve is long enough, then there is no need for glue at the chamfer. The membrane is shown as being slightly flared in FIG. 3 to clarify the drawing. In fact, it is either stopped at the top of the chamfer, or else it is extended beyond the top while being a close fit round the sleeve so as to avoid any excess thickness. The free end 14 of the length 12 is shown closed in the same manner as in the first embodiment by being hot sealed, but it would equally be possible to use a plug.

The chamfer is formed at the end of a metal sleeve using the technique used for sharpening microelectrodes: the end is repeatedly dipped in an acid bath and is subjected to an electrical potential, with protection being provided on the inside or the outside depending respectively on whether an external chamfer or an internal chamfer is required.

The sleeve of the microdialysis probe may also be made in the form of a catheter of flexible plastic material, e.g. made of silicone elastomer (Silastic, registered trademark) because of its full biological compatibility. The dialysis membrane is then mounted at the end of the silicone catheter containing a polyimide capillary, with the flexible sleeve being capable of acting as the other tube for delivery/removal. In this case, the dialysis membrane is tubular, threaded over the silicone sleeve, and glued by epoxy resin. Such a device can perform dialysis at a distance from the point of entry into the organism and is particularly applicable to cardiac dialysis of laboratory animals which no longer need to be immobilized or anesthesized.

The dialysis membrane used may be any conventional membrane, optionally chemically and/or enzymatically modified in order to obtain the desired selectivity or affinity.

Microdialysis probes of the invention may be used for selectively taking samples from the substances excreted in the vicinity of target cells, or for perfusing drugs or medicines in said vicinity, or for perfusing reaction inducers or reaction indicators (markers, radioactive tracers, . . .). This makes it possible to act more directly on a target cell than can be done with conventional administration.

I claim:

1. A microdialysis probe, comprising an outer sleeve having a proximal end region and a distal end region and a transverse seal at said proximal end region, a plurality of tubes extending into said outer sleeve through said seal for delivering and removing dialysis products, said outer sleeve at said distal end region thereof being provided with a circumferential chamfer, and a dialysis membrane cemented to said outer sleeve at said circumferential chamfer of the latter.

2. A microdialysis probe according to claim 1, wherein said circumferential chamfer is directed inwardly of said outer sleeve, said dialysis membrane has the form of a disc with an outwardly directed peripheral chamfer, and said dialysis membrane is located within the confines of said distal end region of said outer sleeve with said peripheral chamfer of the former juxtaposed and cemented to said circumferential chamfer of the latter.

3. A microdialysis probe according to claim 1, wherein said circumferential chamfer is directed outwardly of said outer sleeve, said dialysis membrane has the form of a tube having first and second end regions, and said distal end region of said outer sleeve is received within said first end region of said dialysis membrane, the portion of the interior surface of said dialysis membrane at said first end region thereof which is juxtaposed to said circumferential chamfer of said outer sleeve being cemented to the latter along said circumferential chamfer, and said dialysis membrane being sealed at said second end region thereof.

4. A microdialysis probe, comprising an outer sleeve having a proximal end region and a distal end region and a transverse seal at said proximal end region, a plurality of tubes extending into said outer sleeve through said seal for delivering and removing dialysis products, said outer sleeve at said distal end region thereof being provided with an outwardly directed circumferential chamfer, and a tubular dialysis membrane having first and second end regions and secured to said outer sleeve at said distal end region of the latter, said distal end region of said outer sleeve being received in said first end region of said tubular dialysis membrane with a tight fit, and said tubular dialysis membrane being sealed at said second end region thereof.

5. A microdialysis probe according to claim 4, wherein said outer sleeve is made of flexible plastic material.

* * * * *